United States Patent [19]
Pugia

[11] Patent Number: 5,374,561
[45] Date of Patent: Dec. 20, 1994

[54] OXIDATIVE CREATININE ASSAY

[75] Inventor: Michael J. Pugia, Granger, Ind.

[73] Assignee: Miles Inc., Elkhart, Ind.

[21] Appl. No.: 140,878

[22] Filed: Oct. 25, 1993

[51] Int. Cl.$^5$ ............................................. G01N 33/70
[52] U.S. Cl. ..................... 436/98; 436/810; 436/904; 436/164; 435/4
[58] Field of Search ..................... 422/55–57, 422/82.05, 82.09; 436/96–98, 106, 171, 904, 805, 810; 435/4, 164

[56] References Cited
U.S. PATENT DOCUMENTS

| | | | |
|---|---|---|---|
| 3,710,510 | 1/1973 | Tully et al. | 47/58 |
| 4,004,368 | 1/1977 | Tully | 47/58 |
| 5,173,431 | 12/1992 | Pugia et al. | 436/86 |

OTHER PUBLICATIONS

Hausenbuiller, R. 1978. Soil Science, pp. 73–75; 481–484. William C. Brown, Co.; Dubuque, Iowa.
Black, C. 1968, Soil-Plant Relationships, pp. 92–94. John Wiley & Sons, Inc.; New York.

*Primary Examiner*—David A. Redding
*Attorney, Agent, or Firm*—Jerome L. Jeffers

[57] ABSTRACT

The present invention is a method for the detection of creatinine in an aqueous solution, particularly urine, which involves contacting the solution with a soluble cupric salt, a hydroperoxide and an oxidizable indicator which provides a detectable response in the presence of oxygen free radicals and a pseudoperoxidase. The invention is predicated on the discovery that cupric ions form a complex with creatinine which complex exhibits peroxidase like activity.

10 Claims, 1 Drawing Sheet

OXIDATIVE CREATININE ASSAY

BACKGROUND OF THE INVENTION

Peroxidase is an enzyme that catalyzes the oxidation of various compounds such as phenols and amines, by peroxides. In addition, particular compounds have been termed pseudoperoxides because they behave in a manner similar to the peroxidase enzyme by liberating oxygen from hydroperoxides and transferring the oxygen to certain acceptor compounds. Accordingly, the pseudoperoxides are enzyme-like in that they catalyze, or otherwise participate in, reactions between peroxides and oxidizable compounds. The pseudoperoxides, which include hemoglobin and its derivatives, are regarded as peroxidatively active substances.

For example, in the assay of urine for glucose, the enzyme glucose oxidase, in the presence of oxygen, first converts the glucose in the urine to gluconic acid and hydrogen peroxide after which the peroxidase enzyme which is included in the assay system catalyzes the interaction between the hydrogen peroxide (hydroperoxide) and an oxidizable dye compound, such as o-tolidine or tetramethylbenzidine, to cause the dye, which is colorless in its reduced state, to become colored thereby providing a detectable response. The degree and intensity of the colored response are directly proportional to the amount of hydrogen peroxide generated by the glucose conversion, provided there is sufficient peroxidase present to catalyze the oxidation of the dye.

Similarly, a peroxidatively active substance such as hemoglobin or a derivative thereof can catalyze the interaction between a hydroperoxide and an oxidizable dye. In such interactions, the peroxidatively active substance imitates the peroxidase and catalyzes the interaction between the oxidizable dye and the hydroperoxide. The resulting interaction provides a detectable response, such as a color transition, wherein the intensity of the response is indicative of the concentration of the peroxidatively active substance.

Creatinine is the end metabolite when creatine becomes creatine phosphate and is used as an energy source for muscle contraction. The creatinine produced is filtered by the kidney glomeruli and then excreted into the urine without reabsorption. The determination of creatinine in body fluids is useful for diagnosing muscle diseases or various kidney diseases such as nephritis and renal insufficiency.

The first practical test for the determination of creatinine in urine, known as the Jaffe method, involves the formation of the red-yellowish brown colored creatinine picrate by the bonding of picric acid and creatinine in an alkaline solution. A more recent method for creatinine determination is reported by Benedict and Behre in *J. Biol. Chem.*, 113: 515 (1936) which involves the reaction of 3,5-dinitrobenzoic acid with creatinine in an alkaline medium. Each of these reactions require a high pH, i.e. on the order of 12-13, in order to deprotonate the creatinine, so that the system can operate properly. Strongly basic substances such as alkali and alkaline earth metal hydroxides are typically used to maintain a suitably high pH in these reagent systems. Operating at such a high pH presents various difficulties, especially when an absorbent carrier such as filter paper or a porous film is used as carrier for the reagent system because, upon introduction of the alkali, the carrier tends to become brittle and it is difficult to obtain even distribution of the alkali throughout the carrier matrix. Furthermore, when the reagents are applied to the carrier in the form of a solution and the solvent evaporated to leave a dry residue, the dried alkali does not readily solubilize when contacted with a fluid such as urine which is being examined for creatinine concentration.

The present invention is predicated on the discovery that copper ion and creatinine are able to form a complex which will act as a pseudoperoxidase in the previously described system in which a hydroperoxide in the presence of a peroxidase or pseudoperoxidase oxidizes a chromogenic indicator to provide a detectable response.

In *Polyhedron*, Vol. 4, No. 7, Pp. 1159–1161, 1985; Mitewa et al describe a complex formation between Cu(II) and creatinine. They disclose that a Cu(II) complex with creatinine is formed with a metal:ligand ratio of 1:2 and that complex 4-membered chelate rings are formed which differ significantly from the corresponding Co(II), Cd(II), Zn(II) and Hg(II) complexes.

SUMMARY OF THE INVENTION

The present invention involves a method for the detection of creatinine in an aqueous medium. The method involves contacting the medium suspected of containing creatinine with cupric ions in the presence of a hydroperoxide and a redox indicator which provides a colored response in thee presence of oxygen free radicals.

DESCRIPTION OF THE INVENTION

Figure 1:
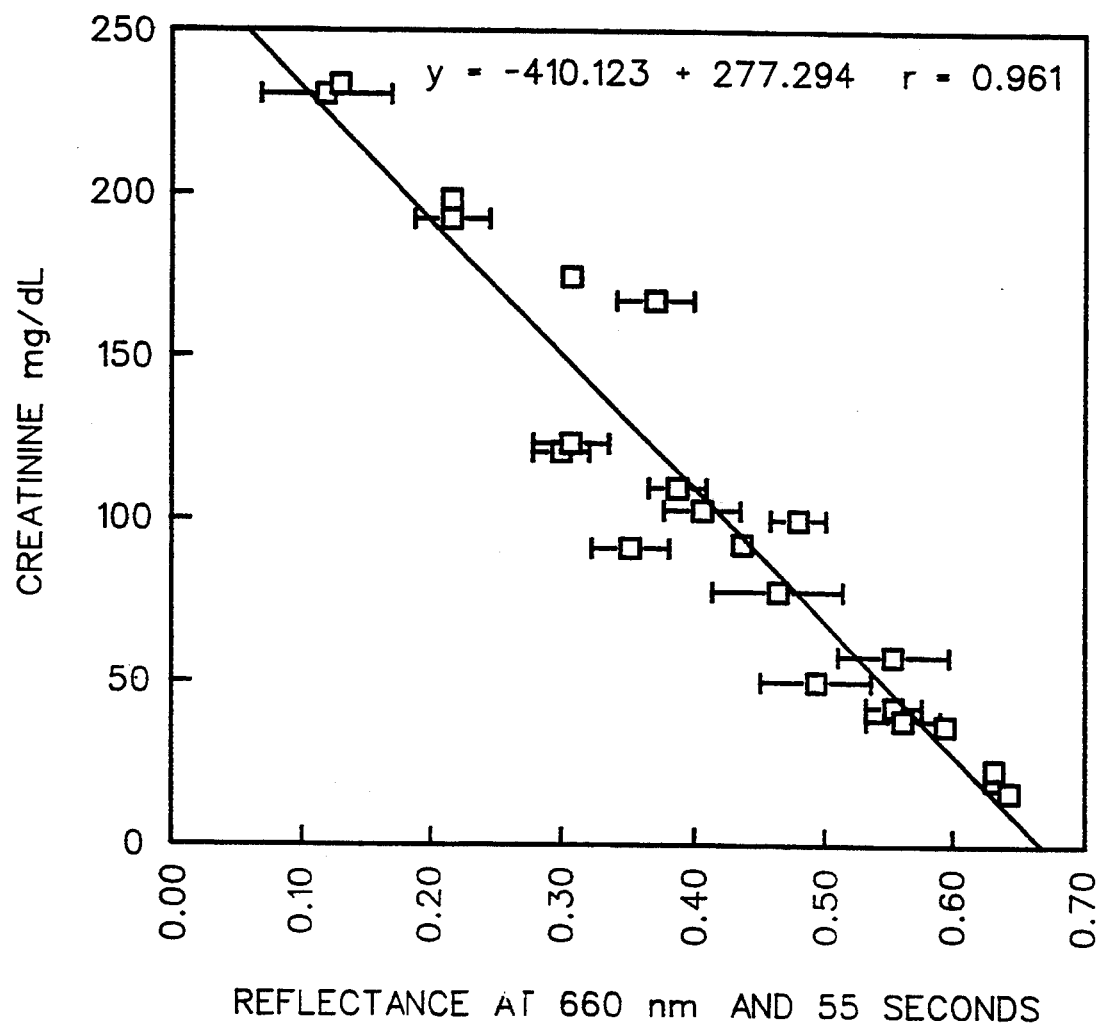
FIG. 1 is a graph of reflectance as a function of creatinine concentration which demonstrates the linearity of response achievable with the present invention.

While the invention is not predicated on any particular mechanism or theory, it is believed that the following set of reactions, in which the copper is in the form of CuII.Citrate and TMB is tetramethylbenzidine, illustrate the present system for the determination of creatinine:

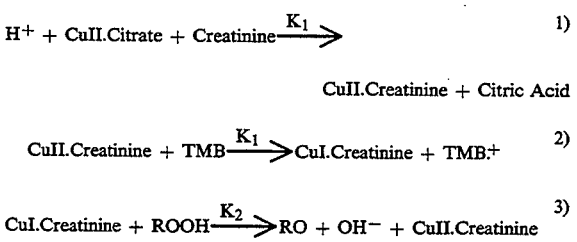

In the foregoing scheme, reaction 1 represents the formation of the Cu.Creatinine complex from its resting state. Reaction 2 represents the oxidation of the TMB dye by the transfer of 1 electron from the TMB to the CuII.Creatinine complex to produce the non-reactive CuI form. Reaction 3 is the regeneration step whereby the CuI complex loses an electron to the peroxide to regenerate the CuII.

Since TMB is in excess and $K_1$ is constant, only the acidity of the solution and the citrate to CuII ratio will influence the amount of CuII.Creatinine produced given a fixed amount of creatinine. Thus, $$[TMB\overset{+}{\cdot}] = k_1[Cu.Creatinine] \cdot [TMB]$$
Blue Color    $k_1$ = constant
Formed    [TMB] = Dye in uncolored form Since $k_1$ is constant and [TMB] is very large, the amount of [CuII.Creatinine] determines the amount of color formed, where $$[CuII.Creatinine] = \frac{K_1[Creatinine][CuII.Citrate][H^+]}{[Citrate]}$$

The [CuII.Creatinine] is dependent on:
(A) $K_1$ = equilibrium constant
(B) $[H^+]$ = the pH. The [CuII.Creatinine] increases as pH decreases or $[H^+]$ increases.
(C) Citrate, as [citrate] increases as the [CuII.Creatinine] decreases yet there must be enough [citrate] to make CuII.Citrate.
(D) If $H^+$ and citrate are fixed, the amount of CuII is dependent only on creatinine.

The source of cupric ion may be any soluble copper salt whose anion does not detrimentally interact with the reaction for the colorimetric detection of creatinine. Suitable salts include copper sulfate, nitrate oxide, hydroxide, phosphate, iodide, chloride, bromide, acetate or oxalate. Other soluble cupric salts may be used provided that they allow formation of the CuII.Creatinine complex. Those salts whose anion binds too strongly to the copper will not allow the copperII.Creatinine complex to be formed. Accordingly, CuII complexes such as those formed between cupric ions and EDTA, HEDTA, EGTA and DTPA would not release sufficient CuII for formation of the CuII.Creatinine complex. It has been observed that the citrate and sulfate salts have the lowest blank reactivity and, accordingly, they are preferred. Cupric citrate is particularly preferred due to its exhibiting the least blank reactivity and the greatest formation of the CuII.Creatinine complex. Salts which oxidize the dye in the absence of creatinine are less desirable. Salts such as cupric 2,2′-bipyridine can cause significant oxidation of TMB in the absence of creatinine, and are, therefore, unsuitable for use in the present invention. When copper citrate is used as the cupric ion source, the concentration of citrate ion should be at least that of copper. An excess of citrate ion of at least twice that of the copper ion is preferred to ensure complete complexation of CuII by the citrate.

Typically, when urine is the aqueous fluid being tested, the concentration of cupric ion will be from 5 to 30 mM since the reference range of creatinine in urine is 3 to 20 mM. This range would vary in other fluids such as serum where one would preferably employ a concentration of cupric ion in the range of from 0.05 to 0.30 mM. The Cuprous ion tends to cause some background interference due to oxidation of the dye in the absence of creatinine. Accordingly, CuI salts cannot be used.

Suitable oxidizable indicators include, for example, benzidine; o-tolidine; a 3,3′,5,5′-tetraalkylbenzidine wherein the alkyl group includes from one to about six carbon atoms; o-dianisidine; 2,7-diaminofluorene; bis-(N-ethylquinol-2-one)-azine; (N-methylbenzthiazol-2-one)-(1-ethyl-3-phenyl-5-methyltriazol-2-one)-azine or combinations thereof.

Suitable hydroperoxides for use in the present invention include cumene hydroperoxide; 5-butyl hydroperoxide; diisopropylbenzene hydroperoxide; 1-hydroxycyclohexane-1-hydroperoxide; 2,5-dimethylhexane-2,5-dihydroperoxide; paramenthane hydroperoxide; 1,4-diisopropylbenzene monohydroperoxide; p-t-butylisopropylbenzene hydroperoxide; 2-(α-hydroperoxyisopropyl)-6-isopropylnaphthalene; tetralin hydroperoxide or combinations thereof.

Typically, the reagent system, comprising the soluble copper salt, hydroperoxide and oxidizable indicator will be dissolved in water. However, organic solvents can be incorporated into the system provided they do not interfere with the assay mechanism. The concentration of the hydroperoxide and oxidizable indicator will normally range from 10 to 150 mM with a range of from 60 to 100 mM being preferred.

In the practice of the invention, the assay can be performed in either the wet or the dry (test strip) format. In carrying out the assay, the test sample is mixed with the copper salt, e.g. cupric citrate, the dye and the hydroperoxide at a buffered pH, preferably from 4.0 to 9.0, through the use of a reagent strip or aqueous and acetonitrile solutions of reagents. Reagent strips are prepared in the conventional manner of dipping an absorbant carrier into an aqueous solution of the cupric salt and buffers, drying the carrier and then dipping it into an organic solution of the dye and hydroperoxide with subsequent drying.

The present invention is further illustrated by the following Examples:

EXAMPLE I

A liquid (wet phase) assay for creatinine was performed by the addition of 0.5 mL of urine to 1.5 mL of an aqueous solution containing 8.4 mM cupric sulfate, 16 mM citrate as the trisodium salt and 250 mM succinic acid buffer to maintain the pH at 7.0. To the solution was added DBDH (100 mM) and TMB (100 mM) in acetonitrile with mixing.

The absorbance at 422 nm was measured at 60 seconds using a Gilford Response II spectrophotometer. Standard solutions were used to prepare a curve relating creatinine concentration to absorbance using Beer's Law; A=EC from which the creatinine concentration in the urine sample was determined.

EXAMPLE II

Dry reagent paper was prepared through sequential impregnations of Whatman BP87 filter paper with an aqueous first dip and an acetonitrile second dip using 3 dryer zones of 60°/60°/60° C. respectively. The first dip contained copper ion in the form of copper sulfate along with citric acid to bind the copper in its resting state and prevent binding by urine proteins as well as to chelate any phosphate, oxylate as well as free amines or ammonium ion present in the urine, and succinic acid as a buffer having low copper binding capability. The second dip contained the redox indicator 3,3′,5,5′ tetramethylbenzidine (TMB) and the hydroperoxide, diisopropylbenzene dihydroperoxide (DBDH).

|  | Concentration mM |
|---|---|
| First Dip (aqueous) | |
| Copper sulfate | 16.0 |
| Citric Acid | 27.0 |
| Succinic Acid | 250.0 |
| Adjust to pH 7.0 with 1 N NaOH | |
| Second Dip (acetonitrile) | |
| 3,3′,5,5′ tetramethylbenzidine (TMB) | 80 |

| -continued | |
| --- | --- |
| | Concentration mM |
| Diisopropylbenzene dihydroperoxide | 90 |

ANALYSIS

Strips were made from papers produced from the above formulation. The reflectance at 660 nm was measured with a Clinitek®-10 spectrophotometer. The reflectance at 600 nm obtained at 45 seconds after dipping the strip in urine containing various levels of creatinine was taken to represent reagent reactivity towards creatinine. Reagent reactivity was determined using 22 individually collected urines whose creatinine values were determined using standard methodology on the Roeche COBAS-FARA instrument, i.e. the Jaffe reaction. The urines tested were distributed across the full specific gravity and pH range.

RESULTS

FIG. 1 is a graph of reflectance as a function of creatinine concentration. While a non-linear dose response was obtained when the reagent result was expressed in K/S values, a linear dose response was obtained when the reagent result was expressed in reflectance values. A good correlation was observed between creatinine values determined using the Jaffe reaction and the reflectance values obtained with the oxidative creatinine reagent of the present invention. The reagent result in urine containing 200 mg/dL creatinine was unaffected by the addition of 50 mg/dL ascorbic acid, indicating no negative inference from ascorbate. Furthermore, the reagent result in a urine sample containing 45 mg/dL creatinine was unaffected by the addition of 0.405 mg/dL hemoglobin, indicating no positive interference at this level of the peroxidatively active hemoglobin. Reagent reactivity increased with decreasing pH. A reagent pH of 7.0 provided the largest reflectance range between samples containing 50 and 250 mg/dL creatinine. Creatinine reactivity was also observed with ferric chloride, however, the high level of interference renders iron unsuitable. Copper was selected because it underwent less interference from urinary components other than creatinine such as phosphate. Citric acid was included to further reduce the influence of ammonium and succinic acid served as a buffer. Other buffers; such as acetate, malonic acid, boric acid, tartaric acid and malic acid; can be used.

The method of this invention is limited to the use of copper ion. Iron shows some creatinine binding ability but is non-specific. In its resting state, iron is not stable to urine components other than creatinine.

What is claimed is:

1. A method for the detection of creatinine in urine which comprises contacting a urine sample suspected of containing creatinine with cupric ions in the presence of citrate, a hydroperoxide and an oxidizable dye which provides a colored response in the presence of oxygen free radicals and a pseudoperoxide wherein the citrate acts to prevent urine components other then creatinine from complexing with the cuptic ions.

2. The method of claim 1 wherein the cupric ions are derived from a soluble cupric salt whose anion is selected from the group consisting of sulfate, nitrate, oxide, hydroxide, phosphate, iodide, chloride, bromide, acetate or oxalate.

3. The method of claim 1 wherein the cupric ion is derived from cupric citrate.

4. The method of claim 3 where in the concentration of citrate ion in the urine sample is at least twice that of the cupric ion.

5. The method of claim 1 wherein the concentration of cupric ions in the urine sample is at least 5 to 30 mM.

6. The method of claim 1 wherein the oxidizable dye is benzidine; o-tolidine, 3,3',5,5'-tetraalkylbenzidine wherein the alkyl groups contain from one to six carbon atoms; o-dianisidine; 2,7-diaminofluorene; bis-(N-ethylquinol-2-one)-azine; (N-methylbenzthiazol-2-one)-( 1-ethyl-3-phenyl-5-methyltriazol-2-one)-azine or a combination thereof.

7. The method of claim 1 wherein the hydroperoxide is cumene hydroperoxide; 5-butyl hydroperoxide; diisopropylbenzene hydroperoxide; 1-hydroxycyclohexane-1-hydroperoxide; 2,5-dimethylhexane-2,5-dihydroperoxide; paramenthane hydroperoxide; 1,4-diisopropylbenzene hydroperoxide; p-t-butyl-isopropylbenzene hydroperoxide; 2-(α-hydroperoxyisopropyl)-6-isopropylnaphthalene; tetralin hydroperoxide or a combination thereof.

8. The method of claim 1 wherein the concentration of the oxidizable dye and the hydroperoxide in the urine sample ranges from 10 to 150 mM.

9. The method of claim 8 wherein the concentration ranges from 60 to 100 mM.

10. The method of claim 1 wherein the cupric ions, hydroperoxide and oxidizable dye are introduced to the urine sample by means of an absorbant test strip to which they have been applied.

* * * * *